United States Patent [19]

Leistner et al.

[11] Patent Number: 4,767,834

[45] Date of Patent: Aug. 30, 1988

[54] VINYL BENZYL 2,2,6,6-TETRAMETHYL PIPERIDINES

[75] Inventors: William E. Leistner, Atlantic Beach, N.Y.; Yutaka Nakahara, Okegawa, Japan; Bunji Hirai; Mitsuharu Kanai, both of Kuki, Japan

[73] Assignee: Adeka Argus Chemical Co., Ltd., Urawa City, Japan

[21] Appl. No.: 28,164

[22] Filed: Mar. 19, 1987

Related U.S. Application Data

[62] Division of Ser. No. 806,251, Dec. 5, 1985, Pat. No. 4,692,485.

[51] Int. Cl.[4] ............... C08F 26/06; C08F 114/02
[52] U.S. Cl. .................. 526/265; 525/331.4; 525/375; 524/99; 524/103; 546/19; 546/216; 546/223
[58] Field of Search ............ 526/265; 525/331.4, 525/375

[56] References Cited

U.S. PATENT DOCUMENTS

| | | | |
|---|---|---|---|
| 3,651,033 | 3/1972 | Armen et al. | 526/265 |
| 4,596,756 | 6/1986 | Yamanouchi et al. | 526/265 |
| 4,692,485 | 9/1987 | Leistner et al. | 524/99 |

Primary Examiner—John Kight, III
Assistant Examiner—Kriellion Morgan

[57] ABSTRACT

Vinyl benzyl 2,2,6,6-tetramethyl piperidines are provided, having the formula:

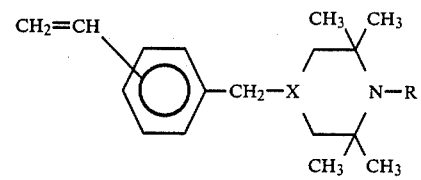

wherein:
R is selected from the group consisting of hydrogen; oxyl; acyl and alkyl having from one to about eighteen carbon atoms;

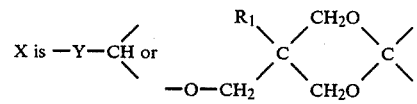

in which Y is —O— or —N($R_2$)—, $R_1$ is alkyl having from one to about eighteen carbon atoms and $R_2$ is hydrogen or alkyl having from one to about eighteen carbon atoms.

2 Claims, No Drawings

VINYL BENZYL 2,2,6,6-TETRAMETHYL PIPERIDINES

This is a division of application Ser. No. 806,251, filed Dec. 15, 1985, now U.S. Pat. No. 4,692,485.

The 2,2,6,6-tetramethyl piperidine compounds are widely used light stabilizers for organic materials.

U.S. Pat. Nos. 3,640,928 and 4,046,737 disclose derivatives of 2,2,6,6-tetramethyl-4-piperidinol. Derivatives of 2,2,6,6-tetramethyl-4-piperidylamine are disclosed in U.S. Pat. No. 3,684,765 and Japanese Pat. No. 7861/80. Derivatives of ketal compounds of 2,2,6,6-tetramethyl-4-piperidone with trimethylol alkanes are disclosed in U.S. Pat. No. 4,212,974.

High molecular weight light stabilizers derived from piperidine compounds having a polymerizable double bond in the molecule are disclosed in U.S. Pat. Nos. 4,210,612, 4,311,820, 4,308,362, 4,404,301, 4,413,096, 4,499,220 and 4,487,887 and Japan Kokai Nos. 137358/82, 157612/80, 38708/83 and 108238/83. These piperidine compounds are derivatives of unsaturated carboxylic acids, alcohols or amines, which are difficult to polymerize.

In accordance with the present invention, vinyl benzyl 2,2,6,6-tetramethyl piperidine compounds are provided having the formula:

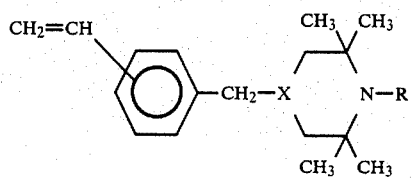

These compounds have an improved light stabilizing effect, and in addition are readily polymerized to form high molecular weight light stabilizers. Therefore, these compounds are also useful monomeric intermediates for the preparation of high molecular weight light stabilizers.

In the above formula:

R is selected from the group consisting of hydrogen; oxyl; acyl and alkyl having from one to about eighteen carbon atoms;

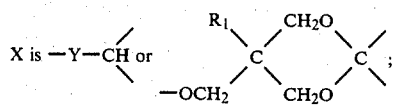

Y is —O— or —N($R_2$)—, in which $R_1$ is alkyl having from one to about eighteen carbon atoms, and $R_2$ is hydrogen or alkyl having from one to about eighteen carbon atoms.

Exemplary R, $R_1$ and $R_2$ alkyl include methyl, ethyl, propyl, isopropyl, butyl, isobutyl, sec-butyl, t-butyl, amyl, isoamyl, sec-amyl, tert-amyl, hexyl, isohexyl, tert-hexyl, heptyl, isoheptyl, sec-heptyl, tert-heptyl, octyl, isooctyl, 2-ethylhexyl, tert-octyl, 1,1,3,3-tetramethylbutyl, nonyl, isononyl, tert-nonyl, decyl, isodecyl, dodecyl, tetradecyl, hexadecyl, and octadecyl.

Exemplary R acyl include formyl, acetyl, propionyl, butyroyl, valeryl, octanoyl, caproyl, lauroyl, myristol, palmitoyl, stearoyl, acryloyl, methacryloyl, benzoyl and toluoyl.

The compounds of this invention can be readily prepared by reaction of vinyl-benzyl chloride with 2,2,6,6-tetramethyl-4-piperidinols; 2,2,6,6-tetramethyl-4-aminopiperidines; or ketal compounds prepared from 2,2,6,6-tetramethyl-4-piperidones and trimethylolkanes.

The following Examples illustrate their preparation.

EXAMPLE I

Preparation of 2,2,6,6-tetramethyl-4-vinylbenzyloxypiperidine 2,2,6,6-Tetramethyl-4-piperidinol 3.93 g was dissolved in 25 ml of dimethylformamide. Sodium hydride 0.66 g was added at room temperature while stirring. After stirring for two hours at room temperature, chloromethylstyrene (meta: 60%, para: 40%) 3.81 g was added dropwise at below 0° C.

After the addition was completed, the solution was stirred for one hour at room temperature, and then an additional one hour at 40° to 50° C.

The solution was then poured into ice water, and extracted with benzene. The benzene solution was washed with water and dried. The solution was evaporated, and 3.79 g of brownish liquid product was obtained.

Results of analysis

High speed liquid chromatography: One peak

NMR (δ value: ppm): 7.33~7.23 (4H), 6.67 (1H), 5.71 (1H), 5.20 (1H), 4.53 (2H), 3.79 (1H), 1.19 (2H) and 1.29~1.11 and 1.17 (14H)

IR ($cm^{-1}$): 3340 (N—H), 1635 (C=C) and 1082 (C—O—C)

|  | Elemental analysis | | |
|---|---|---|---|
|  | C % | H % | N % |
| Calcd.: | 79.07 | 9.95 | 5.12 |
| Found: | 79.25 | 9.88 | 5.07 |

EXAMPLE II

Preparation of 1,2,2,6,6-pentamethyl-4-vinylbenzyloxy piperidine

The procedure of Example I using 1,2,2,6,6-pentamethyl-4-piperidinol 4.25 g instead of 2,2,6,6-tetramethyl-4-piperidinol, yielded 4.46 g of brownish liquid product.

Results of analysis

High speed liquid chromatography: One peak

NMR (δ value: ppm): 7.34~7.23 (4H), 6.65 (1H), 5.70 (1H), 5.19 (1H), 4.51 (2H), 3.65 (1H), 2.23 (3H), 1.87 (2H), 1.51 (2H), 1.17 (6H) and 1.01 (6H)

IR ($cm^{-1}$): 2820 (N—$CH_3$), 1630 (C=C) and 1081 (C—O—C)

| | Elemental analysis | | |
|---|---|---|---|
| | C % | H % | N % |
| Calcd.: | 79.39 | 10.17 | 4.87 |
| Found: | 79.56 | 9.95 | 4.72 |

EXAMPLE III

Preparation of 9-aza-8,8,10,10-tetramethyl-3-ethyl-3-vinylbenzyloxymethyl-1,5-dioxaspiro(5.5)undecane The procedure of Example I using 9-aza-8,8,10,10-tetramethyl-3-ethyl-1,5-dioxaspiro(5.5)-3-undecylmethanol 6.78 g instead of 2,2,6,6-tetramethyl-4-piperidinol yielded 8.53 g of brownish liquid product.

Results of analysis

High speed liquid chromatography: One peak
NMR (δ value: ppm): 7.30~7.16 (4H), 6.64 (1H), 5.71 (1H), 5.19 (1H), 4.47 (2H), 3.63 (4H), 3.49 (2H), 1.72 (2H), 1.60 (2H), 1.45~1.13 and 1.20 (14H) and 0.79 (3H)
IR (cm$^{-1}$): 3250 (N—H), 1631 (C=C) and 1100 (C—O—C)

| | Elemental analysis | | |
|---|---|---|---|
| | C % | H % | N % |
| Calcd.: | 74.38 | 9.62 | 3.61 |
| Found: | 73.52 | 9.56 | 3.70 |

EXAMPLE IV

Preparation of 9-aza-8,8,9,10,10-pentamethyl-3-ethyl-3-vinylbenzyloxymethyl-1,5,-dioxaspiro(5.5)undecane The procedure of Example I using 9-aza-1,8,8,10,10-pentamethyl-3-ethyl-1,5-dioxaspiro(5.5)-3-undecylmethanol 7.13 g instead of 2,2,6,6-tetramethyl-4-piperidinol yielded 8.13 g of brownish liquid product.

Results of analysis

High speed liquid chromatography: One peak
NMR (δ value: ppm): 7.33~7.23 (4H), 6.63 (1H), 5.72 (1H), 5.17 (1H), 4.50 (2H), 3.63 (4H), 3.50 (2H), 2.26 (3H), 1.86 (2H), 1.74 (2H), 1.45~1.07 and 1.14 (14H) and 0.80 (3H)
IR (cm$^{-1}$): 2835 and 2800 (N—CH$_3$), 1635 (C=C) and 1100 (C—O—C)

| | Elemental analysis | | |
|---|---|---|---|
| | C % | H % | N % |
| Calcd.: | 74.77 | 9.79 | 3.49 |
| Found: | 73.85 | 9.64 | 3.62 |

EXAMPLE V

Preparation of 2,2,6,6-tetramethyl-4-N-butyl-N-vinylbenzylaminopiperidine 2,2,6,6-Tetramethyl-4-N-butylaminopiperidine 5.3 g and chloromethylstyrene 4.2 g were dissolved in 25 ml of acetone. Powdered sodium hydroxide 1.1 g was added, and stirred for 10 hours under reflux. Then, 1.6 g of chloromethylstyrene and powdered sodium hydroxide 0.4 g were added, and the mixture stirred for 6 hours under reflux.

Precipitated sodium chloride was filtered off, and the filtrate was evaporated. The residue was dissolved in dichloromethane, and then washed with water and dried. The dichloromethane solution was then evaporated, obtaining 5.7 g of brownish liquid product.

Results of analysis

High speed liquid chromatography: One peak
NMR (δ value: ppm): 7.33~7.16 (4H), 6.60 (1H), 5.67 (1H), 5.15 (1H), 3.57 (2H), 3.03 (1H), 2.44 (2H) and 1.93~0.71, 1.14 and 0.85 (23H)
IR (cm$^{-1}$): 3310 (N—H) and 1633 (C=C)

| | Elemental analysis: | | |
|---|---|---|---|
| | C % | H % | N % |
| Calcd.: | 80.43 | 11.04 | 8.53 |
| Found: | 81.04 | 10.75 | 8.21 |

EXAMPLE VI

Preparation of 2,2,6,6-tetramethyl-4-vinylbenzyloxypiperidine-1-oxyl

The procedure of Example I using 2,2,6,6-tetramethyl-4-hydroxypiperidine-1-oxyl instead of 2,2,6,6-tetramethyl-4-piperidinol yielded 4.35 g of reddish brown liquid product.

Results of analysis

High speed liquid chromatography: One peak
IR (cm$^{-1}$): 1635 (C=C) and 1082 and 1018 (C—O—C)

| | Elemental analysis: | | |
|---|---|---|---|
| | C % | H % | N % |
| Calcd.: | 75.00 | 9.03 | 4.86 |
| Found: | 74.51 | 9.16 | 4.67 |

EXAMPLE VII

Preparation of 1-acetyl-2,2,6,6-tetramethyl-4-vinylbenzyloxypiperidine 2.8 g of 2,2,6,6-tetramethyl-4-vinylbenzyloxypiperidine, obtained in Example I, and 5.1 g of acetyl anhydride were dissolved in 15 ml of xylene. Potassium carbonate 3.4 g and hydroquinone 28 mg were added, and the mixture stirred for 4 hours at 120° C.

The reaction mixture was poured into water, and the xylene solution separated and dried. The solution was evaporated, and 2.1 g of brownish liquid product was obtained.

Results of analysis

NMR (δ value: ppm): 7.31~7.22 (4H), 6.65 (1H), 5.71 (1H), 5.14 (1H), 4.46 (2H), 3.81 (1H), 2.14 (3H) 2.03 (2H), 1.99 (2H), 1.56 (6H) and 1.43 (6H)
IR (cm$^{-1}$): 1630 (C=O) and 1073 (C—O—C)

| | Elemental analysis: | | |
|---|---|---|---|
| | C % | H % | N % |
| Calcd.: | 76.19 | 9.21 | 4.44 |

| -continued |  |  |  |
|---|---|---|---|
| | Elemental analysis: | | |
| | C % | H % | N % |
| Found: | 76.62 | 9.28 | 4.52 |

EXAMPLE VIII

Preparation of 1-acetyl-2,2,6,6-tetramethyl-4-N-butyl-N-vinylbenzylaminopiperidine 6.5 g of 2,2,6,6-tetramethyl-4-N-butyl-N-vinylbenzylaminopiperidine obtained in Example V and 20 g of acetyl anhydride were dissolved in 20 ml of xylene. Potassium carbonate 27 g and hydroquinone 65 mg were added, and the mixture stirred for 4 hours at 115°~120° C.

The reaction mixture was poured into water, and the xylene solution separated and dried. The solution was evaporated, and 3.6 g of brownish liquid product was obtained.

Results of analysis

NMR (δ value: ppm): 7.35~7.18 (4H), 6.57 (1H), 5.68 (1H), 5.16 (1H), 3.59 (2H), 3.00 (1H) and 2.60~1.75 (25H)

IR (cm$^{-1}$): 1635 (C=O)

| | Elemental analysis: | | |
|---|---|---|---|
| | C % | H % | N % |
| Calcd.: | 77.84 | 10.27 | 7.57 |
| Found: | 78.15 | 10.35 | 7.61 |

The compounds of this invention are light stabilizers for organic materials, and intermediates for the preparation of high molecular weight light stabilizers for organic materials.

The vinylbenzyl 2,2,6,6-tetramethyl piperidines or polymers thereof of the invention can be combined with conventional heat stabilizers such as phenolic antioxidant heat stabilizers, thereby constituting light and heat stabilizer compositions of the invention.

The pheolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

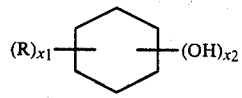

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

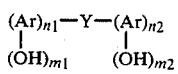

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

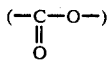

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

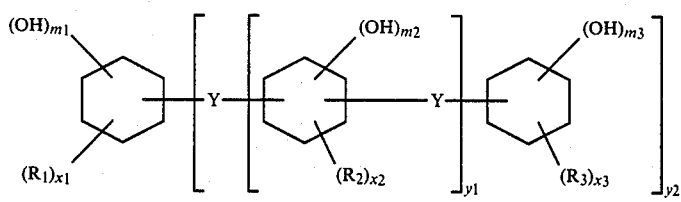

wherein $R_1$, $R_2$ and $R_3$ are inert substituent groups as described in the previous paragraph;

$m_1$ and $m_3$ are integers from one to a maximum of five;

$m^2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

—CH₂—CH₂—; —(CH₂)₅—; —CH₂—;

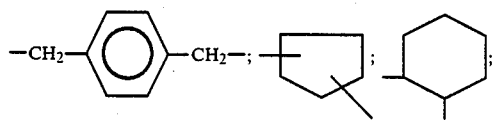

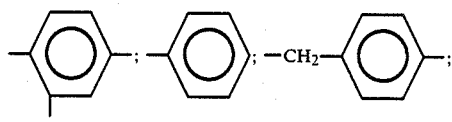

-continued

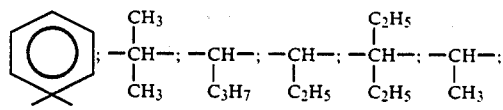

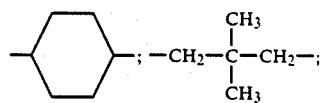

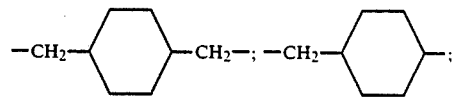

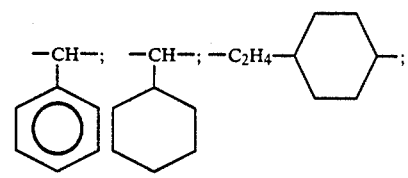

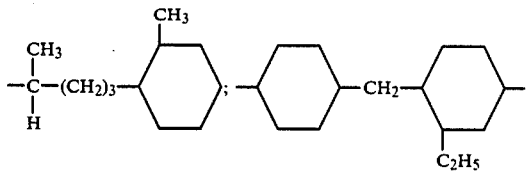

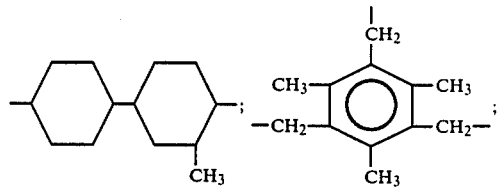

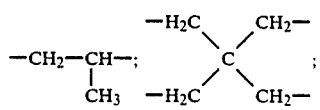

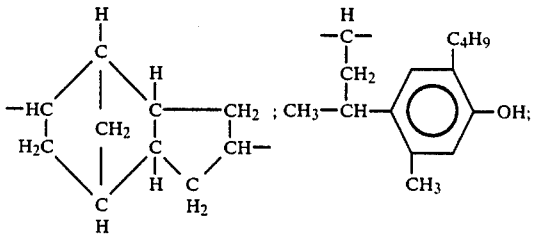

(2) Y groups where only atoms other than carbon link the aromatic rings, such as

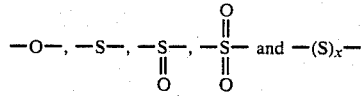

where x is a number from one to ten;

(3) Y groups made of more than a single atom including both carbon and other atoms linking the aromatic nuclei, such as:

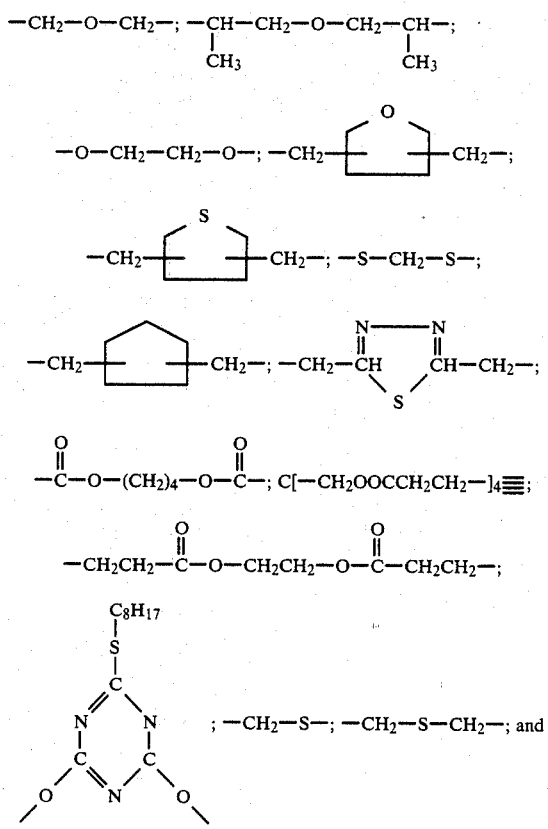

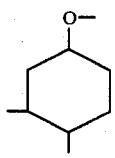

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxyphenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxyphenyl)propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis (naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxyphenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4- hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis [methylene-3 (3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

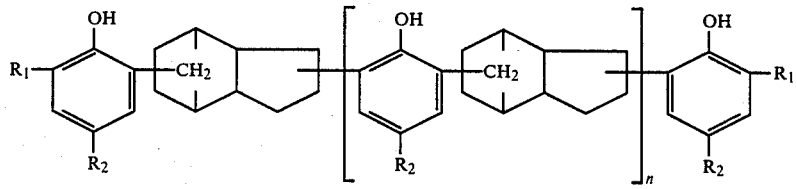

in which

R$_1$ and R$_2$ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commerically available member of this class is Wingstay L, exemplified by dicyclopentadiene tri-(2-tert-butyl-4-methyl-phenol) of the formula:

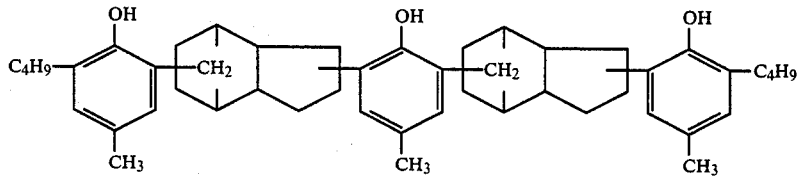

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

In addition, the stabilizer compositions of the invention can include other stabilizers conventionally used as heat and/or light stabilizers for synthetic resins, including polyvalent metal salts of organic acids, organic triphosphites and acid phosphites.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

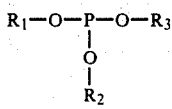

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

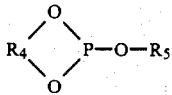

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

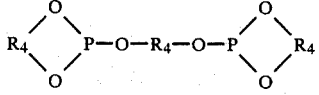

More complex triphosphites are formed from trivalent organic radicals, of the type:

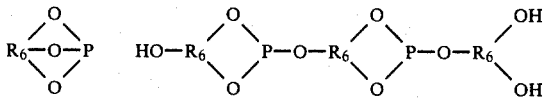

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

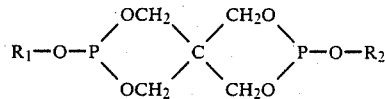

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula;

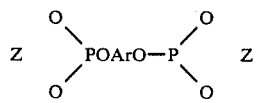

or

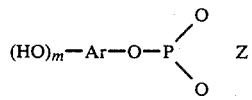

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol diphosphite), 3,9-di(dexyloxy)-2,4,8,10-tetroxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-toyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane, where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-bis(2-tertiary-butyl-5-methylphenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol)-)diphenyl phosphite, isooctyl 2,2'-bis(-para-hydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl-(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methylcyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, triisooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

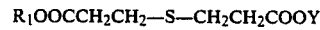

$R_1OOCCH_2CH_2-S-CH_2CH_2COOY$ in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

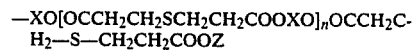

$-XO[OCCH_2CH_2SCH_2CH_2COOXO]_nOCCH_2CH_2-S-CH_2CH_2COOZ$ where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:

(a) $R_1OOCCH_2CH_2SCH_2CH_2COOH$
(b) $R_1OOCCH_2CH_2SCH_2CH_2COOR_2$
(c) $R_1O[OCCH_2CH_2SCH_2CH_2COOX-O]_{n_1}OCCH_2CH_2SCH_2CH_2COOZ$
(d) $R_1OOCCH_2CH_2SCH_2CH_2COOM$

In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

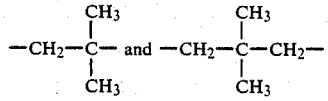

arylene radicals such as phenylene

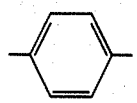

methylenephenylene

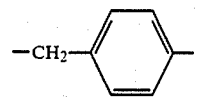

dimethylene phenylene

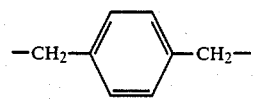

and alicyclylene such as cyclohexylene

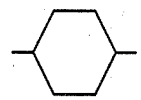

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

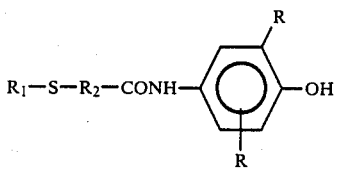

R is alkyl of one to eight carbon atoms, R₁ is alkyl of six to twenty-four carbon atoms, and R₂ is alkylene of one to six carbon atoms.

(2) Thioalkanoic acid amides of 1,3,5-triazines of Ozeki et al Japanese Pat. No. 20,366/68 having the formula:

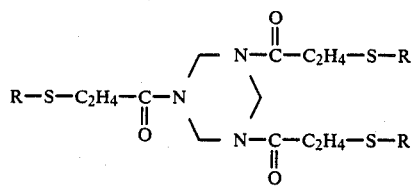

R is alkyl of eight to eighteen carbon atoms.

(3) Bis-thioalkanoic acid amides of Yamamoto et al Japanese Pat. No. 23,765/68 having the formula:

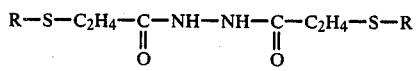

R is alkyl of more than six carbon atoms, aryl or aralkyl.

(4) Bis-thioalkylanoic acid amides of Ozeki et al Japanese Pat. No. 26,184/69 having the formula:

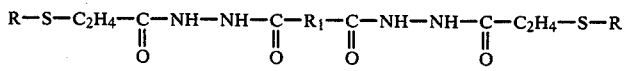

R is alkyl of twelve to eighteen carbon atoms, and R₁ is alkylene of one to ten carbon atoms, cycloalkylene, or arylene.

(5) Bis-alkylene thioalkanoic acid amides of Ozeki Japanese Pat. No. 31,464/69 having the formula:

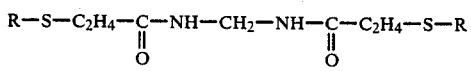

R is alkyl of more than six carbon atoms, aryl, or aralkyl.

(6) Thioalkanoic acid amide derivatives of Minagawa et al, published Japanese application No. 106,484/74 having the formula:

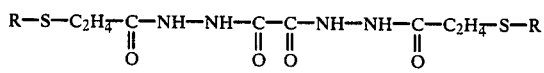

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

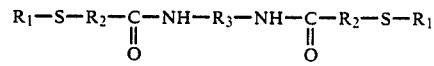

wherein:
R₁ is alkyl having from one to about fifty carbon atoms;
R₂ is alkylene having from one to about three carbon atoms; and
R₃ is alkylene having from about two to about twelve carbon atoms.

β-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)-5-chlorobenzotriazole, 2(2-hydroxy-3,5-di-t-amylphenyl)-benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer composition is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stability including the light stabilizer system of the invention by weight of the polymer are satisfactory. Preferably, from 0.01 to 5% is employed for optimum stabilization.

Inasmuch as all components are solids, the stabilizer systems of the invention are readily rendered in solid particulate form, comprising a blend of:

(a) a heat stabilizer for the synthetic polymer in an amount of from about 10 to about 35 parts by weight;

(b) vinyl benzyl 2,2,6,6-tetramethyl piperidyl compound or polymer thereof in an amount of from about 10 to about 35 parts by weight;

The heat stabilizer is at least one of:

(c) a phenolic antioxidant in an amount from about 10 to about 35 parts by weight; and/or (d) other heat stabilizers in an amount of from about 10 to about 35 parts by weight.

The light stabilizer systems of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer composition is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples represent preferred embodiments of synthetic resin compositions containing the vinyl benzyl 2,2,6,6-tetramethyl piperidines of the invention as light stabilizers.

EXAMPLES 1 TO 8

Polypropylene compositions were prepared using the light stabilizers of this invention and four of prior art, and having following formulation:

| Ingredient | Parts by Weight |
| --- | --- |
| Unstabilized polypropylene | 100 |
| Stearyl-$\beta$-3,5-di-t-butyl-4-hydroxyphenylpropionate | 0.2 |
| Stabilizer | 0.3 |

The compositions were thoroughly blended in a Brabender Plastograph, and then compression-molded to form sheets 0.3 mm thick. Pieces 2.5 cm² were cut off from the sheets, and exposed to a high voltage mercury lamp until failure.

The hours to failure were noted, and shown in Table I.

TABLE I

| Example No. | Stabilizer | Hours to Failure |
| --- | --- | --- |
| Control A | 2,2,6,6-Tetramethyl-4-benzyloxypiperidine | 180 |
| Control B | 1,2,2,6,6-Pentamethyl-4-benzyloxypiperidine | 210 |
| Control C | 2,2,6,6-Tetramethyl-4-benzylaminopiperidine | 160 |
| Control D | 9-Aza-8,8,10,10-tetramethyl-3-ethyl-3-benzyloxymethyl-1,5-dioxaspiro (5.5) undecane | 160 |
| Example 1 | 2,2,6,6-Tetramethyl-4-vinylbenzyloxypiperidine | 420 |
| Example 2 | 1,2,2,6,6-Pentamethyl-4-vinylbenzyloxypiperidine | 440 |
| Example 3 | 9-Aza-8,8,10,10-tetramethyl-3-ethyl-3-vinylbenzyloxymethyl-1,5-dioxaspiro (5.5) undecane | 380 |
| Example 4 | 9-Aza-8,8,10,10-tetramethyl-3-ethyl-3-vinylbenzyloxymethyl-1,5-dioxaspiro (5.5) undecane | 410 |
| Example 5 | 2,2,6,6-Tetramethyl-4-N—butyl-N—vinylbenzylaminopiperidine | 380 |
| Example 6 | 2,2,6,6-Tetramethyl-4-vinylbenzyloxypiperidine-1-oxyl | 430 |
| Example 7 | 1-Acetyl-2,2,6,6-tetramethyl-4-vinylbenzyloxypiperidine | 400 |
| Example 8 | 1-Acetyl-2,2,6,6-tetramethyl-4-N—butyl-N—vinylbenzylaminopiperidine | 360 |

The superiority of the vinyl benzyl piperidines of the invention to like compounds without the vinyl substituent is apparent, upon comparison with the Controls.

The monomeric vinyl benzyl 2,2,6,6-tetramethyl piperidines of the invention form polymers at the vinyl benzyl group when reacted with themselves to form homopolymers, or when reacted with other copolymerizable monomers to form copolymers, all containing the 2,2,6,6-tetramethyl piperidine group, and therefore high molecular weight light stabilizers, capable of improving the resistance of synthetic polymers to deterioration upon exposure to ultraviolet light. Because of their high molecular weight, they are less volatile than the vinyl benzyl monomers from which they are formed, and therefore resistant to volatilization and loss when the polymer is heated.

The polymerization proceeds in the normal way for vinyl polymerization, using the usual vinyl polymer catalysts, and polymerization temperatures. The reaction should be carried out in an inert atmosphere, and, if desired, under superatmospheric pressure.

Other copolymerizable monomers include allyl carboxylic acids and esters, such as acrylic acid, methacrylic acid, methyl acrylate, methyl methacrylate, ethyl acrylate, and ethyl methacrylate; alkyl vinyl ethers having from one to about eighteen carbon atoms, such as methyl vinyl ether, ethyl vinyl ether, propyl vinyl ether, butyl vinyl ether, isopropyl vinyl ether, isobutyl vinyl ether, amyl vinyl ether, hexyl vinyl ether and 2-ethylhexyl vinyl ether; aliphatic carboxylic acid vinyl esters having from two to about eight carbon atoms, such as vinyl acetate, vinyl propionate, vinyl butyrate, vinyl caproate, vinyl caprylate and vinyl 2-ethylhexanoate; triallyl isocyanurate; pinene; tricyclo(5.2.1.0$^{2,6}$)decene-3; maleic and fumaric acid and maleic acid and fumaric acid esters.

The polymerization catalysts or initiators include organic peroxides and organic azonitriles.

In forming copolymers, the molar ratio of vinyl benzyl piperidine to copolymerizable monomer can be within the range from 10:1 to 1:10, preferably 5:1 to 1:5.

The following Example illustrates polymerization of the vinyl benzyl piperidines to prepare high molecular weight light stabilizers.

EXAMPLE 9

9-Aza-8,8,9,10,10-pentamethyl-3-ethyl-3-vinylbenzyloxymethyl-1,5-dioxaspiro(5.5)undecane (prepared in Example IV) 6.1 g, toluene 3.3 g and azo-bis-(isobutyronitrile) 12 mg were stirred at 85° C. for 3 hours under a nitrogen stream.

Methanol 100 ml was added, and the resulting precipitate filtered off and dried. The resulting yellow powder melted at 100°~105° C., and had a molecular weight of about 7000. The polymer was a good light stabilizer, when used in the polypropylene composition of Examples 1 to 8.

Having regard to the foregoing disclosure the following is claimed as the inventive and patentable embodiments thereof:

1. An addition polymer of vinyl benzyl 2,2,6,6-tetramethyl piperidine having the formula:

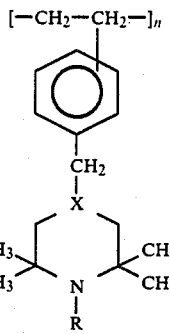

wherein:
n is the number of vinyl benzyl 2,2,6,6-tetramethyl piperidinyl units in the polymer and is a number within the range from 2 to about 10,000;
R is selected from the group consisting of hydrogen; oxyl; acyl and alkyl having from one to about eighteen carbon atoms;
X is —Y—CH or

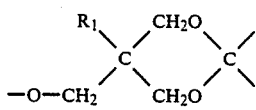

in which Y is —O— or —N($R_2$)—, $R_1$ is alkyl having from one to about eighteen carbon atoms and $R_2$ is hydrogen or alkyl having from one to about eighteen carbon atoms.

2. A polymer of vinyl benzyl 2,2,6,6-tetramethyl piperidine according to claim 1, in which the vinyl benzyl group is in the para position of the benzene ring, R is methyl and X is

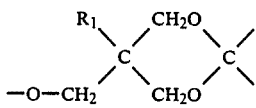

* * * * *